US012758527B2

(12) United States Patent
Williams, Sr.

(10) Patent No.: US 12,758,527 B2
(45) Date of Patent: Oct. 13, 2026

(54) ANTIBACTERIAL COMPOUNDS, PHARMACEUTICAL COMPOSITIONS, AND METHODS OF TREATING BACTERIAL INFECTIONS

(71) Applicant: Miralogx LLC, Tampa, FL (US)

(72) Inventor: Jonnie R. Williams, Sr., Sarasota, FL (US)

(73) Assignee: Miralogx LLC, Tampa, FL (US)

( * ) Notice: Subject to any disclaimer, the term of this patent is extended or adjusted under 35 U.S.C. 154(b) by 200 days.

(21) Appl. No.: 18/828,686

(22) Filed: Sep. 9, 2024

(65) Prior Publication Data

US 2025/0082606 A1 Mar. 13, 2025

Related U.S. Application Data

(60) Provisional application No. 63/537,621, filed on Sep. 11, 2023.

(51) Int. Cl.

| | |
|---|---|
| ***A61K 31/404*** | (2006.01) |
| ***A61K 31/407*** | (2006.01) |
| ***A61K 31/428*** | (2006.01) |
| ***A61K 31/429*** | (2006.01) |
| ***C07D 209/08*** | (2006.01) |
| ***C07D 277/62*** | (2006.01) |
| ***C07D 487/04*** | (2006.01) |
| ***C07D 513/04*** | (2006.01) |

(52) U.S. Cl.

CPC .......... *A61K 31/404* (2013.01); *A61K 31/407* (2013.01); *A61K 31/428* (2013.01); *A61K 31/429* (2013.01); *C07D 209/08* (2013.01); *C07D 277/62* (2013.01); *C07D 487/04* (2013.01); *C07D 513/04* (2013.01)

(58) Field of Classification Search

CPC .. A61K 31/404; A61K 31/407; A61K 31/428; A61K 31/429; C07D 209/08; C07D 277/62; C07D 487/04; C07D 513/04

See application file for complete search history.

(56) References Cited

FOREIGN PATENT DOCUMENTS

DE 2833671 A1 * 2/1980 .......... C07D 513/04

* cited by examiner

*Primary Examiner* — Kamal A Saeed
*Assistant Examiner* — David M Shim
(74) *Attorney, Agent, or Firm* — KellDann Law PLLC; Paul M. Rivard

(57) ABSTRACT

Compounds disclosed herein may exhibit antibacterial and anti-inflammatory properties. Pharmaceutical compositions containing the compound(s) may be used to treat bacterial infections, such as urinary tract infections, and/or disorders associated with chronic inflammation.

7 Claims, No Drawings

ANTIBACTERIAL COMPOUNDS, PHARMACEUTICAL COMPOSITIONS, AND METHODS OF TREATING BACTERIAL INFECTIONS

CROSS REFERENCE TO RELATED APPLICATION

This application claims priority under 35 U.S.C. § 119(e) to U.S. Application No. 63/537,621, filed Sep. 11, 2023, the disclosure of which is hereby incorporated by reference in its entirety.

BACKGROUND

The surfacing of bacterial resistance to a number of antimicrobial agents such as beta-lactam antibiotics, macrolides, quinolones, and vancomycin has become a pervasive health problem. A significant problem in clinical practice is the increased incidence of methicillin-resistant *Staphylococcus aureus* (MRSA) infections. The mounting resistance of the important community acquired pathogen *Streptococcus pneumoniae* to penicillin and other antibacterial agents has become a global health problem. Multi drug-resistant strains of *Mycobacterium tuberculosis* have surfaced in several countries. The emergence and spread of resistant nosocomial and community-acquired pathogens has become a great menace to global public health.

Antibiotics have been increasingly investigated for their anti-inflammatory effects. In the setting of chronic rhinosinusitis, for example, macrolide and tetracycline antibiotics have been trialed for their anti-inflammatory properties. The anti-inflammatory mechanisms of macrolides include the downregulation of proinflammatory genes, improvement of mucociliary function, and decreased neutrophil accumulation. Observational studies provide support for a prolonged trial of macrolide therapy when conventional therapies fail, especially in patients with low serum IgE levels. Tetracyclines exert anti-inflammatory effects by decreasing inflammatory factors, decreasing neutrophil chemotaxis, and decreasing IgE production. Tetracyclines were shown in one study to decrease nasal polyp size but without any lasting symptom improvement. Other antibiotics shown to exhibit anti-inflammatory effects include trimethoprim-sulfamethoxazole and dapsone.

There remains a need for new compounds for treating patients infected with bacteria, particularly the multi drug-resistant bacteria such as MRSA and VRE. It would be particularly desirable to develop new compounds that also exhibit anti-inflammatory properties.

Urinary tract infections (UTIs) are bacterial infections of the urinary tract and are one of the most common conditions for which patients are prescribed antibiotics (Mazzulli, *The Canadian Journal of Urology* 19 (s1): 42-48, 2012). When it affects the lower urinary tract, it is known as a simple cystitis (a bladder infection). When it affects the upper urinary tract, it is known as pyelonephritis (a kidney infection). Symptoms from a lower urinary tract include painful urination and either frequent urination or urge to urinate (or both); while the symptoms of pyelonephritis include fever and flank pain in addition to the symptoms of a lower UTI. In some cases, a painful burning sensation in the urethra may be present even when not urinating.

UTIs are fairly common in the general population with nearly 50% of women (and 12% of men) having at least one UTI in their lifetime, making UTIs the most common bacterial infection in women. UTIs have a high recurrence rate with about 25% of women experiencing a second episode within 6 months of their first UTI (Foxman, *Disease-a-Month* 49 (2): 53-70, 2003). About 15% of all community-prescribed antibiotics in the US are dispensed for UTIs, which is estimated to total over $1 billion annually. Direct and indirect costs due to UTIs total $1.6 billion annually.

UTIs are categorized into uncomplicated and complicated UTIs (cUTI). Uncomplicated UTIs are usually diagnosed in healthy premenopausal women with normal functioning urinary tracts. cUTIs are found in patients with structural or functional abnormalities in their urinary tract who may possess other underlying risk factors such as antibiotic-resistant organisms, comorbid illnesses, or recurrent UTIs. In addition, if a urinary tract infection involves the upper tract, and the person has diabetes mellitus, is pregnant, is male, or immunocompromised, it is considered complicated. To diagnose either an uncomplicated or complicated UTI, a clinician must perform a history and a physical examination and send samples for urinalysis. Acute symptoms consist of urinary frequency, pain or burning on urination, urgency, or foul smelling or cloudy urine. More severe UTIs that involve the upper urinary tract can present additionally with patient discomfort, flank pain, and fever.

SUMMARY

In one aspect, the present disclosure relates to a compound having a structure of Formula (I):

Formula I

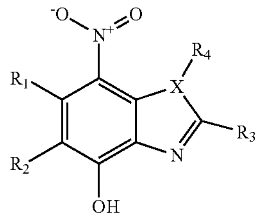

wherein $R_1$, $R_2$, $R_3$, and $R_4$ are each independently selected from the group consisting of an electron pair, H, OH, protected hydroxyl, alkyl, alkenyl, alkynyl, acyl, aryl, heteroaryl, cycloalkyl, phenyl, carbonate ester, a carboxylate, a carboxyl, an ester, a hydroperoxy, a peroxy, an ether, a hemiacetal, a hemiketal, an acetal, a ketal, an orthoester, a methylenedioxy, an orthocarbonate ester, carboxamide, an amine, an imine, an amide, an azide, an azo, a cyanate, a nitrate, a nitrile, an isonitrile, a nitrosooxy, a nitro, a pyridyl, a thiol, a sulfide, sulfinyl, a sulfonyl, a thiocyanate, a carbonothioyl, a phosphate, and heterocycle; optionally wherein the alkyl, alkenyl, alkynyl or acyl is substituted with one or more substituents independently selected from the group consisting of halogen, —OH, alkyl, —O-alkyl, $NR^AR^B$, —S-alkyl, —SO-alkyl, —$SO_2$-alkyl, alkenyl, alkynyl, aryl, heteroaryl, cycloalkyl, and heterocycle; wherein $R^A$ and $R^B$ are each independently selected from hydrogen and $C_{1-4}$ alkyl; wherein the aryl or heteroaryl, whether alone or as part of a substituent group, is optionally substituted with one or more substituents independently selected from the group consisting of halogen, —OH, alkyl, —O-alkyl, —COOH, —C(O)—$C_{1-4}$ alkyl, —C(O)O—$C_{1-4}$ alkyl, $NR^CR^D$, —S-alkyl, —SO-alkyl and —$SO_2$-alkyl; wherein $R^C$ and $R^D$ are each independently selected from hydrogen and $C_{1-4}$ alkyl; wherein X is C or S; or a pharmaceutically acceptable salt or ester thereof. In some embodiments, $R_1$ and $R_2$ form a ring structure.

In some embodiments, the compound has a structure according to Formula (II):

Formula II

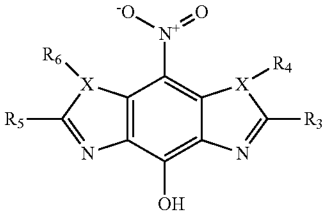

wherein $R_3$, $R_4$, $R_5$, and $R_6$ are each independently selected from the group consisting of an electron pair, H, OH, protected hydroxyl, alkyl, alkenyl, alkynyl, acyl, aryl, heteroaryl, cycloalkyl, phenyl, carbonate ester, a carboxylate, a carboxyl, an ester, a hydroperoxy, a peroxy, an ether, a hemiacetal, a hemiketal, an acetal, a ketal, an orthoester, a methylenedioxy, an orthocarbonate ester, carboxamide, an amine, an imine, an amide, an azide, an azo, a cyanate, a nitrate, a nitrile, an isonitrile, a nitrosooxy, a nitro, a pyridyl, a thiol, a sulfide, sulfinyl, a sulfonyl, a thiocyanate, a carbonothioyl, a phosphate, and heterocycle; optionally wherein the alkyl, alkenyl, alkynyl or acyl is substituted with one or more substituents independently selected from the group consisting of halogen, —OH, alkyl, —O-alkyl, $NR^AR^B$, —S-alkyl, —SO-alkyl, —$SO_2$-alkyl, alkenyl, alkynyl, aryl, heteroaryl, cycloalkyl, and heterocycle; wherein $R^A$ and $R^B$ are each independently selected from hydrogen and $C_{1-4}$ alkyl; wherein the aryl or heteroaryl, whether alone or as part of a substituent group, is optionally substituted with one or more substituents independently selected from the group consisting of halogen, —OH, alkyl, —O-alkyl, —COOH, —C(O)—$C_{1-4}$ alkyl, —C(O)O—$C_{1-4}$ alkyl, $NR^CR^D$, —S-alkyl, —SO-alkyl and —$SO_2$-alkyl; wherein $R^C$ and $R^D$ are each independently selected from hydrogen and $C_{1-4}$ alkyl; wherein X is C or S; or a pharmaceutically acceptable salt or ester thereof.

In some embodiments, X is C. In some embodiments, X is S.

According to one aspect, a novel antibacterial compound has a structure selected from the group consisting of:

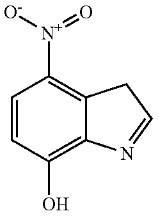

and

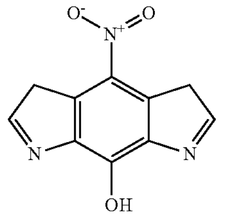

or a pharmaceutically acceptable salt, ester, or solvate thereof.

In some embodiments, the compound has a structure selected from the group consisting of:

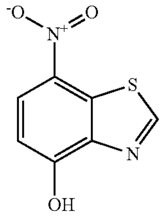

and

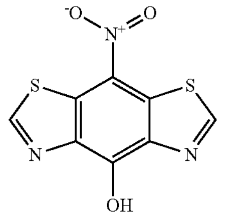

or a pharmaceutically acceptable salt, ester, or solvate thereof.

In another aspect, a pharmaceutical composition comprises a therapeutically effective amount of at least one antibiotic compound depicted above, or a pharmaceutically acceptable salt, ester, or solvate thereof, and a pharmaceutically acceptable vehicle therefor.

In yet another aspect, a method of treating a bacterial infection comprises administering to an individual in need thereof a pharmaceutical composition comprises a therapeutically effective amount of at least one antibiotic compound depicted above, or a pharmaceutically acceptable salt, ester, or ether thereof and a pharmaceutically acceptable vehicle therefor. In some examples, the bacterial infection is a urinary tract infection (UTI), such as an uncomplicated or a complicated UTI.

DETAILED DESCRIPTION

In one aspect, the present disclosure relates to a compound having a structure of Formula (I):

Formula I

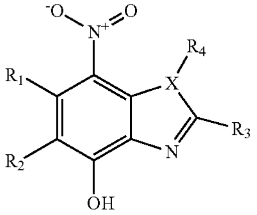

wherein $R_1$, $R_2$, $R_3$, and $R_4$ are each independently selected from the group consisting of an electron pair, H, OH, protected hydroxyl, alkyl, alkenyl, alkynyl, acyl, aryl, heteroaryl, cycloalkyl, phenyl, carbonate ester, a carboxylate, a carboxyl, an ester, a hydroperoxy, a peroxy, an ether, a hemiacetal, a hemiketal, an acetal, a ketal, an orthoester, a methylenedioxy, an orthocarbonate ester, carboxamide, an amine, an imine, an amide, an azide, an azo, a cyanate, a nitrate, a nitrile, an isonitrile, a nitrosooxy, a nitro, a pyridyl, a thiol, a sulfide, sulfinyl, a sulfonyl, a thiocyanate, a carbonothioyl, a phosphate, and heterocycle; optionally wherein the alkyl, alkenyl, alkynyl or acyl is substituted with one or more substituents independently selected from the group consisting of halogen, —OH, alkyl, —O-alkyl, $NR^AR^B$, —S-alkyl, —SO-alkyl, —$SO_2$-alkyl, alkenyl, alkynyl, aryl, heteroaryl, cycloalkyl, and heterocycle; wherein $R^A$ and $R^B$ are each independently selected from hydrogen and $C_{1-4}$ alkyl; wherein the aryl or heteroaryl, whether alone or as part of a substituent group, is optionally substituted with one or more substituents independently selected from the group consisting of halogen, —OH, alkyl, —O-alkyl, —COOH, —C(O)—$C_{1-4}$ alkyl, —C(O)O—$C_{1-4}$ alkyl, $NR^CR^D$, —S-alkyl, —SO-alkyl and —$SO_2$-alkyl; wherein $R^C$ and $R^D$ are each independently selected from hydrogen and $C_{1-4}$ alkyl; wherein X is C or S; or a pharmaceutically acceptable salt or ester thereof. In some embodiments, $R_1$ and $R_2$ form a ring structure.

In some embodiments, the compound has a structure according to Formula (II):

Formula II

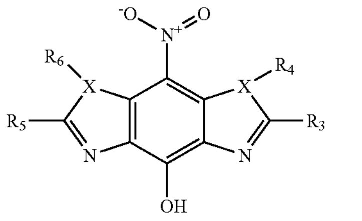

wherein $R_3$, $R_4$, $R_5$, and $R_6$ are each independently selected from the group consisting of an electron pair, H, OH, protected hydroxyl, alkyl, alkenyl, alkynyl, acyl, aryl, heteroaryl, cycloalkyl, phenyl, carbonate ester, a carboxylate, a carboxyl, an ester, a hydroperoxy, a peroxy, an ether, a hemiacetal, a hemiketal, an acetal, a ketal, an orthoester, a methylenedioxy, an orthocarbonate ester, carboxamide, an amine, an imine, an amide, an azide, an azo, a cyanate, a nitrate, a nitrile, an isonitrile, a nitrosooxy, a nitro, a pyridyl, a thiol, a sulfide, sulfinyl, a sulfonyl, a thiocyanate, a carbonothioyl, a phosphate, and heterocycle; optionally wherein the alkyl, alkenyl, alkynyl or acyl is substituted with one or more substituents independently selected from the group consisting of halogen, —OH, alkyl, —O-alkyl, $NR^AR^B$, —S-alkyl, —SO-alkyl, —$SO_2$-alkyl, alkenyl, alkynyl, aryl, heteroaryl, cycloalkyl, and heterocycle; wherein $R^A$ and $R^B$ are each independently selected from hydrogen and $C_{1-4}$ alkyl; wherein the aryl or heteroaryl, whether alone or as part of a substituent group, is optionally substituted with one or more substituents independently selected from the group consisting of halogen, —OH, alkyl, —O-alkyl, —COOH, —C(O)—$C_{1-4}$ alkyl, —C(O)O—$C_{1-4}$ alkyl, $NR^CR^D$, —S-alkyl, —SO-alkyl and —$SO_2$-alkyl; wherein $R^C$ and $R^D$ are each independently selected from hydrogen and $C_{1-4}$ alkyl; wherein X is C or S; or a pharmaceutically acceptable salt or ester thereof. In some embodiments, X is C. In some embodiments, X is S.

According to one aspect, a novel antibacterial compound has a structure selected from the group consisting of:

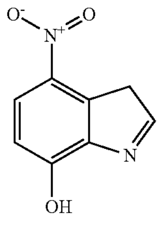

and

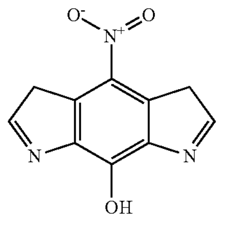

or a pharmaceutically acceptable salt, ester, or solvate thereof.

In some embodiments, the compound has a structure selected from the group consisting of:

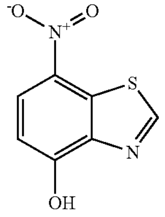

and

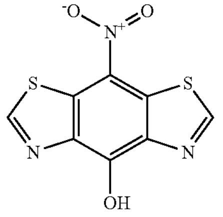

or a pharmaceutically acceptable salt, ester, or solvate thereof.

According to some aspects disclosed herein, a pharmaceutical composition comprises a therapeutically effective dose of at least one antibiotic compound depicted above, or a pharmaceutically acceptable salt, ester, or solvate thereof, and a pharmaceutically acceptable vehicle therefor.

A pharmaceutical composition may include a pharmaceutically acceptable carrier that facilitates processing of an active ingredient into pharmaceutically acceptable compositions. As used herein, the term "pharmacologically acceptable carrier" is synonymous with "pharmacological carrier" and means any carrier that has substantially no long term or permanent detrimental effect when administered and encompasses terms such as "pharmacologically acceptable vehicle," "stabilizer," "diluent," "additive," "auxiliary" or "excipient." Such a carrier generally is mixed with an active compound or permitted to dilute or enclose the active compound and can be a solid, semi-solid, or liquid agent. It is understood that the active ingredients can be soluble or can be delivered as a suspension in the desired carrier or diluent. Any of a variety of pharmaceutically acceptable carriers can be used including, without limitation, aqueous media such as, e.g., water, saline, glycine, hyaluronic acid and the like; solid carriers such as, e.g., mannitol, lactose, starch, magnesium stearate, sodium saccharin, talcum, cellulose, glucose, sucrose, magnesium carbonate, and the like; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active ingredient, its use in pharmaceutically acceptable compositions is contemplated. Non-limiting examples of specific uses of such pharmaceutical carriers can be found in Pharmaceutical Dosage Forms and Drug Delivery Systems (Howard C. Ansel et al., eds., Lippincott Williams & Wilkins Publishers, 7th ed. 1999); REMINGTON: THE SCIENCE AND PRACTICE OF PHARMACY (Alfonso R. Gennaro ed., Lippincott, Williams & Wilkins, 20th ed. 2000); Goodman & Gilman's The Pharmacological Basis of Therapeutics (Joel G. Hardman et al., eds., McGraw-Hill Professional, 10th ed. 2001); and Handbook of Pharmaceutical Excipients (Raymond C. Rowe et al., APhA Publications, 4th edition 2003). These protocols are routine procedures and any modifications are well within the scope of one skilled in the art and from the teaching herein.

According to other aspects disclosed herein, a method of treating a bacterial infection comprises administering to an individual in need thereof a pharmaceutical composition comprises a therapeutically effective dose of the antibiotic compound or a pharmaceutically acceptable salt, ester, or ether thereof and a pharmaceutically acceptable vehicle therefor.

Compounds intended for administration to humans or other mammals generally should have very high purity. Purity refers to the ratio of a compound's mass to the total sample mass following any purification steps. Usually, the level of purity is at least about 95%, more usually at least about 96%, about 97%, about 98%, or higher. For example, the level of purity may be about 98.5%, 99.0%, 99.1%, 99.2%, 99.3%, 99.4%, 99.5%, 99.6%, 99.7%, 99.8%, 99.9%, or higher.

The compounds described herein which exist in more than one optical isomer form (enantiomer) may be provided either as racemic mixture or by isolating one of the enantiomers, the latter case in which purity as described above may refer to enantiomeric purity.

Synthesis of Disclosed Compounds

The compounds may be prepared synthetically using techniques described, for example, in R. Uttamrao Devkar et al., "An Efficient and Alternative method for Synthesis of Nitroxoline," *Asian Journal of Research Chem.*, 12 (2), 69-70 (1988). Alternatively the compounds may be prepared using 8 Hydroxyquinoline as a starting material.

In some aspects, a compound may be converted into a pharmaceutically acceptable salts using techniques well known to persons skilled in the art. For example, salts such as sodium and potassium salts may be prepared by treating the compound with a suitable sodium or potassium base, such as sodium hydroxide or potassium hydroxide, respectively. Esters and ethers of the compound may be prepared as described, e.g., in Advanced Organic Chemistry, 1992, 4th Edition, J. March, John Wiley & Sons, or J. Med. Chemistry, 1992, 35, 145-151.

Methods of Use

The compounds as described herein are particularly useful as antibacterial agents. The compounds may be used, for example, in the treatment of bacterial infections caused by bacteria belonging to *Staphylococcus, Streptococcus, Enterococcus* or *Bacillus* species. *Staphylococcus* species refers to a Gram-positive bacteria, which appears as grape-like clusters when viewed through a microscope and as large, round, golden-yellow colonies, often with β-hemolysis, when grown on blood agar plates. *Staphylococcus aureus* which belongs to *Staphylococcus* species causes a variety of suppurative (pus-forming) infections such as superficial skin lesions such as boils, styes and furunculosis; more serious infections such as pneumonia, mastitis, phlebitis, meningitis, and urinary tract infections; and deep-seated infections, such as osteomyelitis and endocarditis. *Staphylococcus aureus* is a major cause of hospital acquired (nosocomial) infection of surgical wounds and infections associated with indwelling medical devices. *Staphylococcus aureus* causes food poisoning by releasing enterotoxins into food, and toxic shock syndrome by release of superantigens into the blood stream.

*Streptococcus* species refers to a genus of spherical, Gram-positive bacteria, and a member of the phylum Firmicutes. Streptococci are lactic acid bacteria. *Streptococcus* species are responsible for infectious diseases such as meningitis, bacterial pneumonia, endocarditis, erysipelas and necrotizing fasciitis (the 'flesh-eating' bacterial infections).

*Enterococcus* species refers to a genus of lactic acid bacteria of the phylum Firmicutes. They are Gram-positive cocci which often occur in pairs (diplococci). Enterococci are facultative anaerobic organisms. Enterococci are among the most frequent causes of hospital-acquired infections. Enterococci develop resistance to antibiotics such as gentamicin and vancomycin.

*Bacillus* species refers to a large number of diverse, rod-shaped Gram positive bacteria that are motile by peritrichous flagella and are aerobic. It is also a member of the division Firmicutes. Members of this genus are capable of producing endospores that are highly resistant to unfavorable environment conditions. *Bacillus cereus* which belongs to *Bacillus* species causes two types of food-borne intoxications. One type is characterized by the symptoms of nausea, vomiting and abdominal cramps. The second type is manifested primarily by abdominal cramps and diarrhea. Infections attributed to *Bacillus subtilis* which belongs to *Bacillus* species, include bacteremia, endocarditis, pneumonia, and septicemia in patients in compromised immune states.

The compounds disclosed herein may have anti-inflammatory activity. For example, a compound may have an anti-inflammatory activity capable of reducing the levels of an inflammation-inducing molecule. The disclosed compounds may have an anti-inflammatory activity capable of reducing the levels of substance P(SP), calcitonin gene-related peptide (CGRP), glutamate, or a combination thereof. A compound may have an anti-inflammatory activity capable of reducing the levels of SP, CGRP, glutamate, or a combination thereof released from a sensory neuron by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%.

Prostaglandins mediate a local inflammatory response and are involved in all inflammatory functions through action on prostaglandin receptors and mediate inflammatory signaling including chemotaxis (macrophages, neutrophils and eosinophils), vasodilation and algesia. However, the PG-mediated inflammatory response is self-limiting (resolving). The principle resolution factor is a prostaglandin called 15dPGJ2, which is an endogenous agonist of peroxisome proliferator-activator receptor-γ (PPAR-γ) signaling. PPAR-γ signaling pathway 1) induces apoptosis of macrophage M1 cells, thereby reducing the levels of Th1 pro-inflammatory cytokines and 2) promotes differentiation of monocytes into macrophage M2 cells. Macrophage M2 cells produce and release Th2 anti-inflammatory cytokines.

Compounds disclosed herein may have an anti-inflammatory activity capable of reducing the levels of an inflammation inducing prostaglandin. A compound may have an anti-inflammatory activity capable of reducing the levels of an inflammation inducing prostaglandin released from a sensory neuron by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. A compound may have an anti-inflammatory activity capable of reducing the levels of an inflammation inducing prostaglandin released from a sensory neuron in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

The peroxisome proliferator-activated receptors (PPARs) are a group of nuclear receptor proteins that function as transcription factors regulating the expression of genes. All PPARs are known to heterodimerize with the retinoid X receptor (RXR) and bind to specific regions on the DNA of target genes called peroxisome proliferator hormone response elements (PPREs). PPARs play essential roles in the regulation of cellular differentiation, development, and metabolism (carbohydrate, lipid, protein), and tumorigenesis of higher organisms. The family comprises three members, PPAR-α, PPAR-γ, and PPAR-δ (also known as PPAR-β). PPAR-α is expressed in liver, kidney, heart, muscle, adipose tissue, as well as other tissues. PPAR-δ is expressed in many tissues but markedly in brain, adipose tissue, and skin. PPAR-γ comprises three alternatively-spliced forms, each with a different expression pattern. PPAR-γ1 is expressed in virtually all tissues, including heart, muscle, colon, kidney, pancreas, and spleen. PPAR-γ2 is expressed mainly in adipose tissue. PPAR-γ3 is expressed in macrophages, large intestine, and white adipose tissue. Endogenous ligands for the PPARs include free fatty acids and eicosanoids. PPAR-γ is activated by PGD2 (a prostaglandin), whereas PPAR-α is activated by leukotriene B4.

A compound may have an anti-inflammatory activity capable of reducing the levels of IFN-γ, TNF-α, IL-12, or a combination thereof released from a Th1 cell and increasing the levels of IL-10 released from a Th2 cell. A compound may have an anti-inflammatory activity capable of reducing the levels of IFN-γ, TNF-α, IL-12, or a combination thereof released from a Th1 cell by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%, and capable of increasing the levels of IL-10 released from a Th2 cell by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%.

A compound may have an anti-inflammatory activity capable of stimulating some or all PPAR signaling pathways. It is contemplated that such a compound therefore may act as a PPAR pan-agonist or possibly as a selective PPAR agonist.

A compound may have an anti-inflammatory activity capable of modulating Th1 and Th2 cytokines. A compound may have an anti-inflammatory activity capable of reducing the levels of Interferon-γ (IFN-γ), tumor necrosis factor-α (TNF-α), interleukin-12 (IL-12), or a combination thereof released from a Th1 cell. A compound may have an anti-inflammatory activity capable of reducing the levels of IFN-γ, TNF-α, IL-12, or a combination thereof released from a Th1 cell by, e.g., at least 10%, at least 20%, at least 30%, at least 40%, at least 50%, at least 60%, at least 70%, at least 80%, or at least 90%. A compound may have an anti-inflammatory activity capable of reducing the levels of IFN-γ, TNF-α, IL-12, or a combination thereof released from a Th1 cell in a range from, e.g., about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, or about 10% to about 90.

A compound may have an anti-inflammatory activity capable of increasing the levels of IL-10 released from a Th2 cell. A compound may have an anti-inflammatory activity capable of increasing the levels of IL-10 released from a Th2 cell by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%.

Pharmaceutical Compositions and Administration

Compositions as described herein may be administered orally, nasally, topically, subcutaneously, intramuscularly, intravenously, or by other modes of administration.

A pharmaceutical composition may optionally include, without limitation, other pharmaceutically acceptable components (or pharmaceutical components), including, without limitation, buffers, preservatives, tonicity adjusters, salts, antioxidants, osmolality adjusting agents, physiological substances, pharmacological substances, bulking agents, emulsifying agents, wetting agents, sweetening or flavoring agents, and the like. Various buffers and means for adjusting pH can be used to prepare a pharmaceutical composition disclosed herein, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole and butylated hydroxytoluene. Useful preservatives include, without limitation, benzalkonium chloride, chlorobutanol, thimerosal, phenylmercuric acetate, phenylmercuric nitrate, a stabilized oxy chloro composition and chelants, such as, e.g., DTPA or DTPA-bisamide, calcium DTPA, and CaNaDTPA-bisamide. Tonicity adjustors useful in a pharmaceutical composition include, without limitation, salts such as, e.g., sodium chloride, potassium chloride, mannitol or glycerin and other pharmaceutically acceptable tonicity adjustor. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a pharmaceutical composition.

Examples of auxiliaries and/or excipients that may be mentioned are cremophor, poloxamer, benzalkonium chloride, sodium lauryl sulfate, dextrose, glycerin, magnesium stearate, polyethylene glycol, starch, dextrin, lactose, cellulose, carboxymethylcellulose sodium, talc, agar-agar, mineral oil, animal oil, vegetable oil, organic and mineral waxes, paraffin, gels, propylene glycol, benzyl alcohol, dimethylacetamide, ethanol, polyglycols, tween 80, solutol HS 15, and water. It is also possible to administer the active substances as such, without vehicles or diluents, in a suitable form, for example, in capsules.

A pharmaceutical composition may comprise a therapeutic compound in an amount sufficient to allow customary administration to an individual. A unit dose form may have, e.g., at least 5 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, or at least 100 mg of a therapeutic compound. In other aspects, a unit dose form may have, e.g., at least 200 mg, at least 300 mg, at least 400 mg, at least 500 mg, at least 600 mg, at least 700 mg, at least 800 mg, at least 900 mg, at least 1,000 mg, at least 1,100 mg, at least 1,200 mg, at least 1,300 mg, at least 1,400 mg, or at least 1,500 mg of a therapeutic compound. In yet other aspects of this embodiment, a pharmaceutical composition disclosed herein may include, e.g., about 5 mg to about 100 mg, about 10 mg to about 100 mg, about 50 mg to about 150 mg, about 100 mg to about 250 mg, about 150 mg to about 350 mg, about 250 mg to about 500 mg, about 350 mg to about 600 mg, about 500 mg to about 750 mg, about 600 mg to about 900 mg, about 750 mg to about 1,000 mg, about 850 mg to about 1,200 mg, or about 1,000 mg to about 1,500 mg of a therapeutic compound. In still other aspects of this embodiment, a pharmaceutical composition disclosed herein may include, e.g., about 10 mg to about 250 mg, about 10 mg to about 500 mg, about 10 mg to about 750 mg, about 10 mg to about 1,000 mg, about 10 mg to about 1,500 mg, about 50 mg to about 250 mg, about 50 mg to about 500 mg, about 50 mg to about 750 mg, about 50 mg to about 1,000 mg, about 50 mg to about 1,500 mg, about 100 mg to about 250 mg, about 100 mg to about 500 mg, about 100 mg to about 750 mg, about 100 mg to about 1,000 mg, about 100 mg to about 1,500 mg, about 200 mg to about 500 mg, about 200 mg to about 750 mg, about 200 mg to about 1,000 mg, about 200 mg to about 1,500 mg, about 5 mg to about 1,500 mg, about 5 mg to about 1,000 mg, or about 5 mg to about 250 mg of a therapeutic compound.

Pharmaceutical compositions as described herein may include a pharmaceutically acceptable solvent. A solvent is a liquid, solid, or gas that dissolves another solid, liquid, or gaseous (the solute), resulting in a solution. Solvents useful in the pharmaceutical compositions include, without limitation, a pharmaceutically acceptable polar aprotic solvent, a pharmaceutically acceptable polar protic solvent and a pharmaceutically acceptable non-polar solvent. A pharmaceutically acceptable polar aprotic solvent includes, without limitation, dichloromethane (DCM), tetrahydrofuran (THF), ethyl acetate, acetone, dimethylformamide (DMF), acetonitrile (MeCN), dimethyl sulfoxide (DMSO). A pharmaceutically acceptable polar protic solvent includes, without limitation, acetic acid, formic acid, ethanol, n-butanol, 1-butanol, 2-butanol, isobutanol, sec-butanol, tert-butanol, n-propanol, isopropanol, 1,2 propan-diol, methanol, glycerol, and water. A pharmaceutically acceptable non-polar solvent includes, without limitation, pentane, cyclopentane, hexane, cyclohexane, benzene, toluene, 1,4-dioxane, chloroform, n-methyl-pyrrolidone (NMP), and diethyl ether.

The method of administration as well as the dosage range which are suitable in a specific case depend on the species to be treated and on the state of the respective condition or disease, and may be optimized using techniques known in the art. Most often, the daily dose of active compound in a patient is 0.0005 mg to 15 mg per kg, more usually 0.001 mg to 7.5 mg per kg. Dosing can be single dosage or cumulative (serial dosing), and can be readily determined by one skilled in the art. For instance, treatment of a bacterial infection may comprise a one-time administration of an effective dose of a pharmaceutical composition as disclosed herein. Alternatively, treatment may comprise multiple administrations of an effective dose of a pharmaceutical composition carried out over a range of time periods, such as, e.g., once daily, twice daily, trice daily, once every few days, or once weekly. The timing of administration can vary from individual to individual, depending upon such factors as the severity of an individual's symptoms. For example, an effective dose of a pharmaceutical composition disclosed herein can be administered to an individual once daily for an indefinite period of time, or until the individual no longer requires therapy. A person of ordinary skill in the art will recognize that the condition of the individual can be monitored throughout the course of treatment and that the effective amount of a pharmaceutical composition disclosed herein that is administered can be adjusted accordingly.

Pharmaceutical compositions may contain any conventional non-toxic pharmaceutically-acceptable carriers, adjuvants or vehicles. In some cases, the pH of the formulation may be adjusted with acceptable pharmaceutical or food grade acids, bases or buffers to enhance the stability of the formulated composition or its delivery form.

Liquid dosage forms for oral administration include acceptable pharmaceutical or food grade emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylsulfoxide (DMSO) dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include capsules, tablets, lozenges, pills, powders, and granules. In such solid dosage forms, the active compound is mixed with at least one inert, acceptable pharmaceutical or food grade excipient or carrier such as sodium citrate or dicalcium phosphate and/or a) fillers or extenders such as starches, lactose, sucrose, glucose, mannitol, and silicic acid, b) binders such as carboxymethylcellulose, alginates, gelatin, polyvinylpyrrolidone, sucrose and acacia, c) humectants such as glycerol, d) disintegrating agents such as agaragar, calcium carbonate, potato or tapioca starch, alginic acid, certain silicates, and sodium carbonate, e) solution retarding agents such as paraffin, f) absorption accelerators such as quaternary ammonium compounds, g) wetting agents such as cetyl alcohol and glycerol monostearate, h) absorbents such as kaolin and bentonite clay, i) lubricants such as talc, calcium stearate, magnesium stearate, solid polyethylene glycols, sodium lauryl sulfate, and mixtures thereof, and j) sweetening, flavoring, perfuming agents, and mixtures thereof. In the case of capsules, lozenges, tablets and pills, the dosage form may also comprise buffering agents.

The solid dosage forms of tablets, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract or, optionally, in a delayed or extended manner. Examples of embedding compositions which can be used include polymeric substances and waxes. Tablet formulations for extended release are also described in U.S. Pat. No. 5,942,244.

Compositions may contain a compound as disclosed herein, alone or with other therapeutic compound(s). A therapeutic compound is a compound that provides pharmacological activity or other direct effect in the diagnosis, cure, mitigation, treatment, or prevention of disease, or to affect the structure or any function of the body of man or animals. A therapeutic compound disclosed herein may be used in the form of a pharmaceutically acceptable salt, solvate, or solvate of a salt, e.g., a hydrochloride. Additionally, therapeutic compound disclosed herein may be provided as racemates, or as individual enantiomers, including the R- or S-enantiomer. Thus, the therapeutic compound disclosed herein may comprise a R-enantiomer only, a S-enantiomer only, or a combination of both a R-enantiomer and a S-enantiomer of a therapeutic compound. In some aspects, the therapeutic compound may have anti-inflammatory activity, such as a non-steroidal anti-inflammatory drug (NSAID). NSAIDs are a large group of therapeutic compounds with analgesic, anti-inflammatory, and anti-pyretic properties. NSAIDs reduce inflammation by blocking cyclooxygenase. NSAIDs include, without limitation, aceclofenac, acemetacin, actarit, alcofenac, alminoprofen, amfenac, aloxipirin, aminophenazone, antraphenine, aspirin, azapropazone, benorilate, benoxaprofen, benzydamine, butibufen, celecoxib, chlorthenoxacin, choline salicylate, clometacin, dexketoprofen, diclofenac, diflunisal, emorfazone, epirizole; etodolac, etoricoxib, feclobuzone, felbinac, fenbufen, fenclofenac, flurbiprofen, glafenine, hydroxylethyl salicylate, ibuprofen, indometacin, indoprofen, ketoprofen, ketorolac, lactyl phenetidin, loxoprofen, lumiracoxib, mefenamic acid, meloxicam, metamizole, metiazinic acid, mofebutazone, mofezolac, nabumetone, naproxen, nifenazone, niflumic acid, oxametacin, phenacetin, pipebuzone, pranoprofen, propyphenazone, proquazone, protizinic acid, rofecoxib, salicylamide, salsalate, sulindac, suprofen, tiaramide, tinoridine, tolfenamic acid, valdecoxib, and zomepirac.

NSAIDs may be classified based on their chemical structure or mechanism of action. Non-limiting examples of NSAIDs include a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclooxygenase (COX) inhibitor, a selective cyclooxygenase-1 (COX-1) inhibitor, and a selective cyclooxygenase-2 (COX-2) inhibitor. An NSAID may be a profen. Examples of a suitable salicylate derivative NSAID include, without limitation, acetylsalicylic acid (aspirin), diflunisal, and salsalate. Examples of a suitable p-amino phenol derivative NSAID include, without limitation, paracetamol and phenacetin. Examples of a suitable propionic acid derivative NSAID include, without limitation, alminoprofen, benoxaprofen, dexketoprofen, fenoprofen, flurbiprofen, ibuprofen, indoprofen, ketoprofen, loxoprofen, naproxen, oxaprozin, pranoprofen, and suprofen. Examples of a suitable acetic acid derivative NSAID include, without limitation, aceclofenac, acemetacin, actarit, alcofenac, amfenac, clometacin, diclofenac, etodolac, felbinac, fenclofenac, indometacin, ketorolac, metiazinic acid, mofezolac, nabumetone, naproxen, oxametacin, sulindac, and zomepirac. Examples of a suitable enolic acid (oxicam) derivative NSAID include, without limitation, droxicam, isoxicam, lornoxicam, meloxicam, piroxicam, and tenoxicam. Examples of a suitable fenamic acid derivative NSAID include, without limitation, flufenamic acid, mefenamic acid, meclofenamic acid, and tolfenamic acid. Examples of a suitable selective COX-2 inhibitors include, without limitation, celecoxib, etoricoxib, firocoxib, lumiracoxib, meloxicam, parecoxib, rofecoxib, and valdecoxib.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

While the invention has been described with respect to specific examples, those skilled in the art will appreciate that there are numerous variations and permutations of the above described systems and techniques that fall within the spirit and scope of the invention as set forth in the appended claims.

What is claimed is:

1. A compound according to Formula (II):

Formula (II)

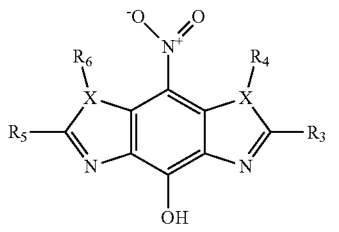

wherein $R_3$, $R_4$, $R_5$, and $R_6$ are each independently selected from the group consisting of an electron pair, H, OH, protected hydroxyl, alkyl, alkenyl, alkynyl, acyl, aryl, heteroaryl, cycloalkyl, phenyl, carbonate ester, a carboxylate, a carboxyl, an ester, a hydroperoxy, a peroxy, an ether, a hemiacetal, a hemiketal, an acetal, a ketal, an orthoester, a methylenedioxy, an orthocarbonate ester, carboxamide, an amine, an imine, an amide, an azide, an azo, a cyanate, a nitrate, a nitrile, an isonitrile, a nitrosooxy, a nitro, a pyridyl, a thiol, a sulfide, sulfinyl, a sulfonyl, a thiocyanate, a carbonothioyl, a phosphate, and heterocycle; optionally wherein the alkyl, alkenyl, alkynyl or acyl is substituted with one or more substituents independently selected from the group consisting of halogen, —OH, alkyl, —O-alkyl, $NR^AR^B$, —S-alkyl, —SO-alkyl, —$SO_2$-alkyl, alkenyl, alkynyl, aryl, heteroaryl, cycloalkyl, and heterocycle; wherein $R^A$ and $R^B$ are each independently selected from hydrogen and $C_{1-4}$ alkyl; wherein X is C or S; or a pharmaceutically acceptable salt or ester thereof.

2. The compound of claim 1, wherein X is C.

3. The compound of claim 1, wherein X is S.

4. The compound of claim 2, wherein the compound is:

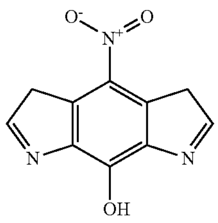

, or a pharmaceutically acceptable salt, ester, or solvate thereof.

5. The compound of claim 3, wherein the compound is:

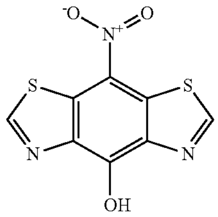

, or a pharmaceutically acceptable salt, ester, or solvate thereof.

6. A pharmaceutical composition comprising an effective amount of the compound of claim 1 and a pharmaceutically acceptable vehicle thereof.

7. A method of treating a bacterial infection comprising administering to an individual in need thereof the pharmaceutical composition of claim 6, wherein the bacterial infection is a urinary tract infection.

* * * * *